United States Patent [19]

Thomaschefsky et al.

[11] 4,047,534
[45] Sept. 13, 1977

[54] NURSING PAD

[75] Inventors: Susan N. Thomaschefsky, Menasha; Ann Sprangers, Appleton, both of Wis.

[73] Assignee: Kimberly-Clark Corporation, Neenah, Wis.

[21] Appl. No.: 756,347

[22] Filed: Jan. 3, 1977

[51] Int. Cl.$^2$ .............................................. A41C 3/00
[52] U.S. Cl. .................................................. 128/461
[58] Field of Search ............... 128/461, 505, 464, 280; 156/290; 428/198

[56] References Cited

U.S. PATENT DOCUMENTS 2,617,102  6/1959  London ................................ 128/461
3,855,046  12/1974  Hansen et al. ....................... 428/198

Primary Examiner—Werner H. Schroeder
Assistant Examiner—Doris L. Troutman
Attorney, Agent, or Firm—Daniel J. Hanlon, Jr.; William D. Herrick; Raymond J. Miller

[57] ABSTRACT

A nursing pad of multi-ply construction that is conformable and comfortable with a high resistance to strike-through and low sticking properties. The pad includes a lightweight layer of thermoplastic polymeric microfibers on one side of an absorbent middle layer containing thermoplastic polymeric fibers and, on the opposite side of the middle layer, a lightweight spunbonded continuous filament thermoplastic polymer layer. The microfiber layer provides resistance to strike-through and will tend to cling to many fabrics preventing displacement of the pad during normal use. The continuous filament layer provides comfort and strength with a reduced tendency to stick. The combination is bonded by embossing wherein the embossing pattern on the microfiber side occupies a lower percentage of the surface area than the bonding pattern on the continuous filament side.

7 Claims, 2 Drawing Figures

NURSING PAD

BACKGROUND OF THE INVENTION

1. Field of the Invention

During the latter stages of pregnancy and after childbirth it is very common for a mother to produce excess milk resulting in varying degrees of leaking which frequently causes discomfort and may result in garment staining. For nursing mothers this problem is prolonged and lasts generally throughout the nursing period. To alleviate these problems it has become common to pad the mother's garments with absorbent material to collect the excess milk. The present invention is directed to an improved pad for this purpose as well as for other related uses which will be apparent.

2. Description of the Prior Art

Nursing pads are presently commercially available and have been otherwise described in the prior art. However, to date, nursing pads have tended to be thick and bulky, detracting from the appearance of the wearer. Furthermore, the bulk of these prior art pads also necessitates some cupping or other forming measure in order to produce a pad that will conform to the wearer so that undue leaking may be prevented. These forming measures may result in a harsh, stiff edge around the pad that can cause chafing or other irritation. Other drawbacks of prior art pads include sticking to the wearer, slipping or displacement from the garment in use, and a lack of breathability resulting in additional discomfort to the wearer. Such prior art pads and others are described, for example, in the following U.S. Pat. Nos. 2,553,825 to Langs issued May 22, 1951; 2,609,539 to Shearer issued Sept. 9, 1952; 2,617,102 to MacHenry issued Nov. 11, 1952; 2,891,544 to London issued June 23, 1959; and 3,156,924 to Wonacott issued Nov. 17, 1964.

Pattern bonded continuous filament webs are also well-known and described in various prior art references. For example, U.S. Pat. No. 3,855,046 to Hansen et al issued Dec. 17, 1974, assigned to the assignee of the present invention, described such webs and a method of making them. Furthermore, it is known to form webs of synthetic, thermoplastic polymeric microfibers. For example, work done at the Naval Research Laboratories in Washington, D. C. is described by Van A. Wendt in an article entitled "Superfine Thermoplastic Fibers" appearing in *Industrial and Engineering Chemistry*, Volume 48, Number 8, Pages 1342 through 1346. It is also known to combine these microfiber webs with other layers or components to form products such as are described in U.S. Pat. No. 3,837,995 to Floden issued Sept. 24, 1974, assigned to the assignee of the present invention, and U.S. Pat. No. 3,916,447 to Thompson issued Nov. 4, 1975, assigned to the assignee of the present invention. The formation of absorbent webs containing a mixture of absorbent fibers such as cellulose and polymeric synthetic fibers has been accomplished by various forming methods.

While each of these individual components is known, the present invention provides a nursing pad that combines these elements in a manner producing benefits which alleviate to a great degree the drawbacks of the prior art nursing pads, especially those relating to appearance and comfort as well as staining.

SUMMARY OF THE INVENTION

The nursing pad of the present invention combines an absorbent inner layer including a proportion of synthetic thermoplastic polymeric fibers sufficient for bonding with a lightweight outer layer of synthetic thermoplastic polymeric microfibers and a second layer on the opposite side of the absorbent layer including a lightweight, spunbonded, continuous filament, thermoplastic synthetic polymeric web. The combination has a basis weight generally in the range of from about 165 g/yd$^2$ to 335 g/yd$^2$ and preferably in the range of from about 220 g/yd$^2$ to 245 g/yd$^2$ and is thin enough to be conformable without requiring it to be formed as a shaped structure. The layers are preferably combined by double embossing with heat and low pressure in a manner such that the spunbonded layer has embossments covering a higher percentage of the surface area than the microfiber layer. In use, the microfiber layer is placed adjacent the wearer's garment and substantially prevents staining resulting from strike-through. The more heavily embossed continuous filament layer on the opposite surface achieves a reduced tendency to produce striking and the accompanying discomfort.

The result is a unique and highly improved combination that can be produced and marketed economically and yet avoids many of the drawbacks and disadvantages of the prior art nursing pads.

DESCRIPTION OF THE PREFERRED EMBODIMENTS

Figure 1:
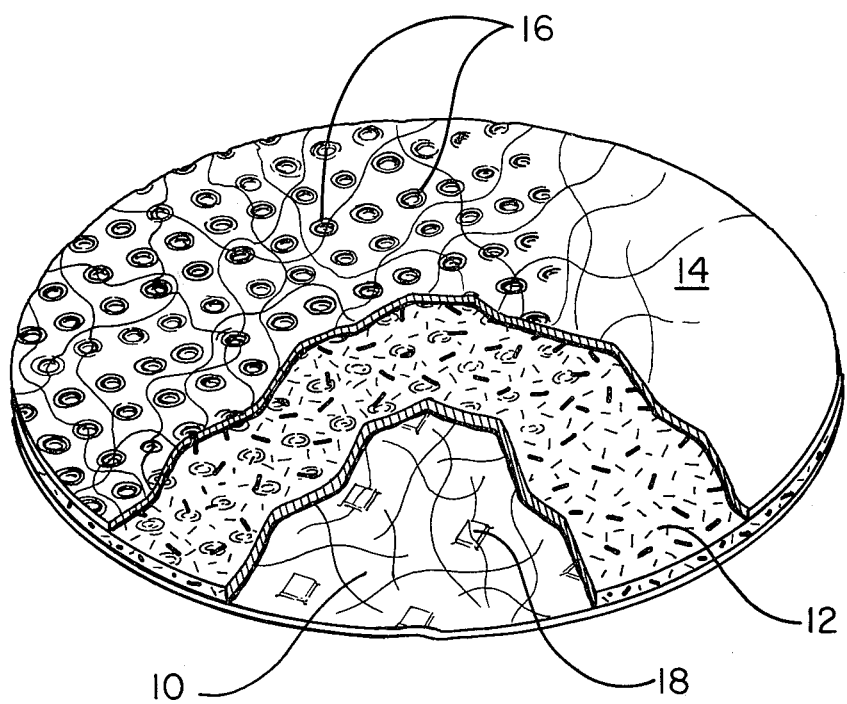
FIG. 1 illustrates a nursing pad of the present invention, partially broken away to reveal the component layers and viewed from the continuous filament side.

While the invention will be described in connection with preferred embodiments, it will be understood that it is not intended to limit the invention to those embodiments. On the contrary, it is intended to cover all alternatives, modifications and equivalents as may be inclued within the spirit and scope of the invention as defined by the appended claims.

As used herein, the reference to "microfiber webs" is to nonwoven webs having a basis weight in the range of from about 0.2 oz/yd$^2$ to about 1.5 oz/yd$^2$ and preferably in the range of from about 0.45 oz/yd$^2$ to 0.75 oz/yd$^2$ and formed of thermoplastic, synthetic polymeric fibers having an average diameter of up to 10 microns. These webs are preferably formed by melt blowing as described in the above mentioned article by Van A. Wendt and are formed of synthetic resins having a softening point perferably in the range of from about 135° to 150° F, particularly polyolefins and especially polypropylene. The term "spunbonded webs" as used herein refers to continuous filament nonwoven webs having a basis weight in the range of from about 0.25 oz/yd$^2$ to 1.5 oz/yd$^2$ and preferably in the range of from about 0.4 oz/yd$^2$ to 0.75 oz/yd$^2$. These webs are formed of a synthetic thermoplastic polymer having a melting point compatible with the temperature required for the thermoplastic polymer in the microfiber web and generally in the range of from about 160° F to 165° F. Preferred thermoplastic polymers are the polyolefins and especially polypropylene and polyethylene. As used herein, the term "absorbent web" refers to a web composed of absorbent cellulosic fibers and thermoplastic polymeric fibers. The content of the thermoplastic fibers is preferably in the range of from about 30 to 50% by weight for the desired combination of strength and absorbency, and the basis weight of the absorbent web is in the range of from about 150 g/yd$^2$ to about 250 g/yd$^2$ and preferably in the range of from about 195 g/yd$^2$ to about 205 g/yd$^2$. The melting point of the thermoplastic polymer component is compatible with the melting points of the thermoplastic polymers utilized in the microfiber and spunbonded layers and is preferably in the range of from about 135° F to about 150° F. Preferred thermoplastic polymers include the polyolefins and especially polypropylene and polyethylene.

Bonding of the component layers is accomplished under conditions of temperature and pressure sufficient to soften the thermoplastic materials in the layers and cause them to bond. Preferably, the embossing takes place by passing the component layers through a patterned nip maintained at the required temperature and pressure. While the selection of a specific temperature or pressure, it will be understood, may be from a wide range depending upon the polymers in the component layers, the pressure is preferably in the range of from about 5 psi to 15 psi, and the temperature is preferably in the range of from about 260° F to about 280° F for polyolefins, for example.

Embossing of the combined components is carried out in a manner to achieve bonding while retaining the non-slip benefits of the microfiber layer and enhancing the non-stick properties of the spunbonded layer. With this in mind, the percent embossment coverage of the microfiber layer is preferably in the range of about 1% to 5% while the percent embossment coverage of the spunbonded layer is preferably in the range of about 10% to 20%.

After embossing the individual nursing pads are preferably formed by die cutting which results in softer edges, but may be formed by other operations such as punching or the like. While the particular pad shape is not critical, they are preferably formed as circles having a diameter in the range of from about 3¾ to 5 inches and preferably in the range of from 4 to 4¾ inches.

For even greater absorbency, if desired, a wetting agent can be incorporated into either or both of the spunbonded or absorbent layers.

EXAMPLE

A nursing pad was formed in accordance with the present invention by combining an outer spunbonded polypropylene layer with a middle layer including wood fibers and polypropylene fibers and further utilizing a second outer layer of polypropylene microfibers. The spunbonded layer was formed in accordance with U.S. Pat. No. 3,855,046 by continuously extruding thermoplastic polypropylene filaments from a melt through a spinnerette and drawing the filaments pneumatically to orient the filaments and achieve tenacity. The filaments were collected in a random manner on a carrier belt to form the web. This web was integrated by pattern bonding in compacted areas. Such webs are available from Kimberly-Clark Corporation under the trademark "EVOLUTION". The spunbonded web utilized in the nursing pad of this example had a basis weight of 0.45 oz/yd$^2$.

The microfiber web was formed by melt blowing polypropylene as described in the Van A. Wendt article above-mentioned and further described in U.S. Pat. No. 3,948,241 to Buntin et al issued Nov. 19, 1974, the disclosure of which is incorporated herein by reference.

The microfiber web had a basis weight of 0.6 oz/yd$^2$.

The absorbent layer was formed by utilizing the melt blowing process described and incorporating wood pulp fibers into the melt blowing air stream. The absorbent web included 40% polypropylene fibers and 60% cellulose fibers by weight. The basis weight of the absorbent web was 200 g/yd$^2$.

The three components were combined by double embossing between two sets of two plates, the first set was maintained at a temperature of 275° F and pressure of 5 psi to bond the spunbonded layer to the absorbent web, and the second set at a temperature of 260° F and pressure of 10 psi to bond all three layers. The time of exposure to each set was about 0.01 second. The embossing on the microfiber web side was of individual square embossments, each having an area of 0.01 in$^2$ and spaced apart by one inch vertically and horizontally for a percent area coverage of 1%. Embossments on the spunbonded side each had an area of 0.01 in$^2$ and were spaced apart by a distance of about ¼ inch (adjacent pegs) or ⅜ inch (diagonal pegs) for a total area embossed coverage of 15%.

The nursing pads were formed by die cutting circles from the sheet of embossed material, each circle having an area of 15.94 in$^2$. The resulting nursing pads had the following properties: absorbency capacity of 22 g. (694% of pad weight), thickness 5/16 in., impermeability (of microfiber web layer) of 60 + min., abrasion resistance of 133 revolutions (spunbonded side, wet) and 51 revolutions (meltblown side, dry), and breathability of 20 ft$^3$/min/ft$^2$. These test procedures are described below.

Absorbency was determined by weighing a dry pad, dipping pad in a plastic basket for 3 minutes in a container 4 inches deep and 6 inches in diameter providing a Similac$^R$ infant formula bath maintained at 30° C ± 1° C, removing the pad and allowing it to drain for 10 minutes, and weighing the sample. The absorbency is reported as the difference between the wet and dry weights of the pad divided by the dry pad weight. Thickness was determined with a probe bulk tester. Permeability was determined in accordance with the standard Mason jar procedure (DART 80.9-70 Tentative) plus a water resistance hydrostatic pressure test (AATCC Text Method 127-1971); breathability was determined with a Fazier Air Permeability tester in accordance with permeability to Air, Cloth, Calibrated Orifice Method, Federal Test Method Standard 191, Method 5450.1. Abrasion resistance was determined in accordance with the Taber Abrasion test by federal Test Method Standard 191, Method 5306 with a CS32 wheel and a 125 g. counterweight; wet tests were run to pilling while dry tests were run to sample destruction.

Figure 2:
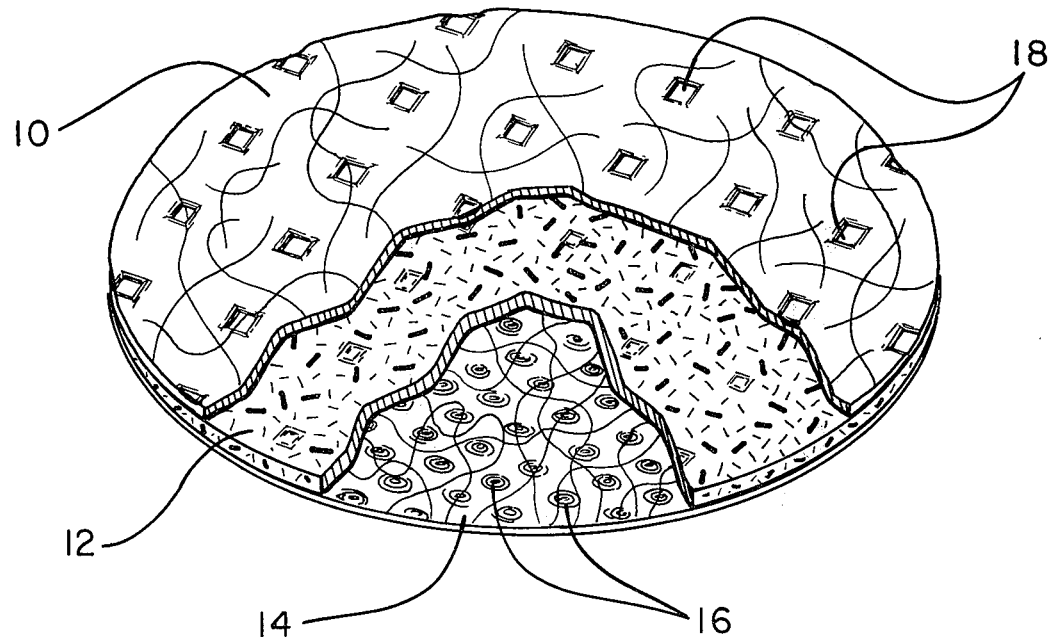
FIG. 2 similarly illustrates the nursing pad of FIG. 1 viewed from the opposite, microfiber layer side.

Turning to FIGS. 1 and 2, the nursing pad to the invention as illustrated by the Example will be further described. As shown, microfiber layer 10 is combined with absorbent layer 12 and spunbonded layer 14. Embossments 18 on the microfiber side 10 occupy less percent area than embossments 16 on spunbonded side 14.

Thus it is apparent that there has been provided, in accordance with the invention, a nursing pad that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications and variations as fall within the spirit and broad scope of the appended claims.

We claim:

1. A flexible, breathable nursing pad having low stick properties, consisting essentially of, a layer having a basis weight of from about 0.2 oz/yd² to 1.5 oz/yd² of synthetic polymeric microfibers having an average fiber diameter of up to 10 microns and a tendency to cling to garments containing natural fibers and a resistance to the passage of aqueous liquids of at least 60 min. according to the Mason jar test, an absorbent middle layer comprising 30 to 50% polymeric fibers by weight and having a basis weight from about 150 g/yd² to about 250 g/yd², and a spunbonded continuous synthetic polymeric filament layer having a basis weight of from about 0.25 oz/yd² to 1.5 oz/yd² on the other side of said absorbent layer opposite from said microfiber layer, said combination being bonded by means of embossments wherein the embossing pattern on the microfiber side occupies from about 1% to 5% of the surface area and the embossing pattern on the continuous filament side occupies from about 10% to 20% of the surface area.

2. The nursing pad of claim 1 wherein the microfibers are polypropylene having a softening point in the range of from 135° F to 150° F.

3. The nursing pad of claim 1 wherein the absorbent layer comprises a mixture of polypropylene fibers having a softening point in the range of from 135° F to 150° F and natural cellulose fibers.

4. The nursing pad of claim 1 wherein the spunbonded layer comprises polypropylene having a softening point in the range of from about 160° F to 165° F.

5. The nursing pad of claim 1 wherein the thermoplastic material used to form the microfiber layer, the spunbonded layer and the polymeric component of the absorbent layer is polypropylene having a softening point in the range of from about 135° F to 150° F.

6. A nursing pad comprising, an absorbent layer having a basis weight of from about 150 g/yd² to 250 g/yd² and comprising a mixture of absorbent, natural cellulose fibers with thermoplastic fibers and containing from about 30 to 50 percent thermoplastic fibers by weight, on one side of said absorbent layer a nonwoven cover having a basis weight of from about 0.25 oz/yd² to 1.5 oz/yd² formed from thermoplastic filaments having a porosity of from about 600 to 900 to 900 ft³/min/ft², on the other side of said absorbent layer a nonwoven cover having a basis weight of from about 0.2 oz/yd² to 1.5 oz/yd² formed from thermoplastic microfibers having a water resistance at least 60 minutes according to the Mason jar test, said layers being interbonded by the application of heat and pressure in spaced areas wherein the spaced areas on the microfiber side cover 1 to 5 percent of the total area and the spaced areas on the opposite side cover 10 to 20 percent of the total area.

7. The nursing pad of claim 6 wherein the thermoplastic material used to form the nonwoven covers and the thermoplastic fibers in the absorbent layer is polypropylene having a softening point in the range of from about 135° F to 150° F.

* * * * *

UNITED STATES PATENT AND TRADEMARK OFFICE
CERTIFICATE OF CORRECTION

PATENT NO. : 4,047,534

DATED : September 13, 1977

INVENTOR(S) : Susan Thomaschefsky and Ann Sprangers

It is certified that error appears in the above-identified patent and that said Letters Patent are hereby corrected as shown below:

Column 2, line 24, "striking" should read -- sticking --.

Column 2, line 43, "inclued" should read -- included --.

Column 3, line 54, "layerof" should read -- layer of --.

Column 4, line 2, "3,948,241" should read -- 3,849,241 --.

Column 4, line 48, "Text" should read -- Test --.

Column 4, line 57, "to" (second occurrence) should read -- of --.

Column 4, line 62, "embossements" should read -- embossments --.

Column 6, line 18, "to 900" second occurrence should be deleted.

Signed and Sealed this

Twenty-first Day of March 1978

[SEAL]

Attest:

RUTH C. MASON
Attesting Officer

LUTRELLE F. PARKER
Acting Commissioner of Patents and Trademarks